(12) United States Patent
Fathi et al.

(10) Patent No.: US 9,901,638 B2
(45) Date of Patent: Feb. 27, 2018

(54) COMPOSITION AND METHOD FOR TREATING AN AUTOIMMUNE DISEASE

(71) Applicant: RedHill Biopharma Ltd., Tel Aviv (IL)

(72) Inventors: Reza Fathi, Hohokus, NJ (US); Patrick Laughlin McLean, Montreal (CA); Harry Jefferson Leighton, Rockport, ME (US)

(73) Assignee: RedHill Biopharma Ltd., Tel Aviv (IL)

( * ) Notice: Subject to any disclaimer, the term of this patent is extended or adjusted under 35 U.S.C. 154(b) by 0 days.

(21) Appl. No.: 14/345,839

(22) PCT Filed: Sep. 19, 2012

(86) PCT No.: PCT/IB2012/002252
§ 371 (c)(1),
(2) Date: Mar. 19, 2014

(87) PCT Pub. No.: WO2013/041963
PCT Pub. Date: Mar. 28, 2013

(65) Prior Publication Data
US 2014/0228307 A1 Aug. 14, 2014

Related U.S. Application Data

(60) Provisional application No. 61/536,824, filed on Sep. 20, 2011, provisional application No. 61/537,229, filed on Sep. 21, 2011.

(51) Int. Cl.
| | | |
|---|---|---|
| A61K 31/435 | (2006.01) | |
| A61K 31/438 | (2006.01) | |
| A61K 31/498 | (2006.01) | |
| A61K 31/7048 | (2006.01) | |
| A61K 45/06 | (2006.01) | |
| A61K 9/48 | (2006.01) | |

(52) U.S. Cl.
CPC ............ *A61K 45/06* (2013.01); *A61K 9/4866* (2013.01); *A61K 31/435* (2013.01); *A61K 31/438* (2013.01); *A61K 31/498* (2013.01); *A61K 31/7048* (2013.01)

(58) Field of Classification Search
CPC .............. A61K 31/7048; A61K 31/435; A61K 31/498; A61K 45/06
See application file for complete search history.

(56) References Cited

U.S. PATENT DOCUMENTS

| | | | | |
|---|---|---|---|---|
| 6,277,836 B1 * | 8/2001 | Borody | ...................... | 514/159 |
| 7,488,580 B1 | 2/2009 | Naser | | |
| 2008/0275063 A1 | 11/2008 | Schauerte et al. | | |
| 2009/0054380 A1 * | 2/2009 | Greenstein | ............. | A61K 31/60 514/161 |
| 2010/0330156 A1 * | 12/2010 | Liu et al. | ...................... | 424/450 |
| 2011/0059136 A1 | 3/2011 | Borody | | |

FOREIGN PATENT DOCUMENTS

| | | |
|---|---|---|
| JP | 2001-524951 A | 12/2001 |
| JP | 2011-511012 A | 4/2011 |
| WO | 98/43667 A1 | 10/1998 |
| WO | 2009/097651 A1 | 8/2009 |
| WO | 2011/011706 A2 | 1/2011 |

OTHER PUBLICATIONS

Selby, W. et al., Gastroenterology, "Two-Year Combination Antibiotic Therapy With Clarithromycin, RIfabutin and Clofazimine for Crohn's Disease", 2007, vol. 132, 2313-2319.*
International Search Report from International Appln. No. PCT/IB2012/002252 dated Mar. 18, 2013.
Ren et al., "Clofazimine Inhibits Human Kv1.3 Potassium Channel by Perturbing Calcium Oscillation in T Lymphocytes", PLos ONE, Dec. 2008, vol. 3, Issue 12, e4009, pp. 1-11.
Wen et al., "Inflammatory Bowel Disease: Autoimmune or Immune-mediated Pathogenesis", Clinical & Developmental Immunology, Sep./Dec. 2004, vol. 11 (3/4), pp. 195-204.
Cossu et al., "Association of *Mycobacterium avium* subsp. paratuberculosis with Multiple Sclerosis in Sardinian Patients", PLos ONE, Apr. 2011, vol. 6, Issue 4, e18482, pp. 1-6.
Dow, "Mycobacterium paratuberculosis and autism: Is this a trigger?", Medical Hypotheses, Dec. 2011, vol. 77, No. 6, pp. 977-981.
Borody et al., "Anti-mycobacterial therapy in Crohn's disease heals mucosa with longitudinal scars", Digestive and Liver Disease 39 (2007) pp. 438-444.
Selby et al., "Two-Year Combination Antibiotic Therapy With Clarithromycin, Rifabutin, and Clofazimine for Crohn's Disease", Gastroenterology Jun. 2007; vol. 132, No. 7, pp. 2313-2319.
Written Opinion issued in Chilean Patent Application No. 201400671 dated Jun. 20, 2016.
Written Opinion issued in Singapore Patent Application No. 11201400386R dated Mar. 16, 2016.
Supplementary European Search Report from European Patent Application No. 12834382.9 dated Jan. 23, 2015.
Tsaregorodtseva et al., "Cytokines in diseases of the digestive system", RLS Medication Guide, Apr. 28, 2009.

* cited by examiner

*Primary Examiner* — Shaojia A Jiang
*Assistant Examiner* — Bahar Craigo
(74) *Attorney, Agent, or Firm* — Greenberg Traurig, LLP

(57) ABSTRACT

A combination of antibiotics including rifabutin, clarithromycin and clofazimine for the treatment of an autoimmune disease such as multiple sclerosis and related diseases. In a further aspect, there is provided a composition comprising a combination of two or more antibiotic agents for the treatment of an autoimmune disease, said two or more antibiotic agents selected from rifabutin, clofazimine, and at least one macrolide.

11 Claims, 12 Drawing Sheets

COMPOSITION AND METHOD FOR TREATING AN AUTOIMMUNE DISEASE

CROSS REFERENCE TO RELATED APPLICATIONS

The present application is a national phase filing under 35 U.S.C. 371 of International Application No. PCT/IB2012/002252, filed on Sep. 19, 2012, which claims the benefit of priority to U.S. provisional application Ser. No. 61/536,824, filed Sep. 20, 2011 and to U.S. provisional application Ser. No. 61/537,229, filed Sep. 21, 2011 all of which are incorporated herein by reference in their entirety.

FIELD OF THE DISCLOSURE

The present disclosure relates to the use of a composition for the treatment of an autoimmune disease. More specifically, the composition comprises a combination of antibiotics which may be used to treat autoimmune diseases including multiple sclerosis

BACKGROUND

Multiple sclerosis (MS) is a chronic autoimmune and demyelinating disease that primarily affects the central nervous system. MS is characterised by the infiltration of myelin-specific CD4+ T cells that attack the axonal myelin sheath and other elements of the central nervous system (CNS), destroying myelin and the basal axon.

The present inventors have found that a combination of antibiotics, previously used in the treatment of inflammatory bowel disorders have an effect on the inflammatory response of a subject suffering from an autoimmune disease including MS and other autoimmune diseases.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY OF THE DISCLOSURE

The disclosure provides a combination of rifabutin, clarithromycin, and clofazimine for the treatment of an auto-immune disease The disclosure, in one aspect, provides a composition including rifabutin, clarithromycin, and clofazimine for the treatment of an auto-immune disease.

The present disclosure also provides a composition including rifabutin, clarithromycin, and clofazimine for the treatment of multiple sclerosis.

In a further aspect, there is provided a composition comprising rifabutin, clarithromycin and clofazimine for the treatment of an autoimmune disease.

In a further aspect, there is provided a composition comprising rifabutin, clarithromycin and clofazimine for the treatment of multiple sclerosis (MS).

In a further aspect, there is provided a composition comprising a combination of antibiotic agents for the treatment of multiple sclerosis, said composition comprising rifabutin, clarithromycin and clofazimine.

In a further aspect, there is provided a composition comprising a combination of two or more antibiotic agents for the treatment of an autoimmune disease, said two or more antibiotic agents selected from rifabutin, clofazimine and at least one macrolide.

In a further aspect, there is provided a composition comprising a combination of two or more antibiotic agents for the treatment of an autoimmune disease, said two or more antibiotic agents selected from rifabutin, clofazimine and clarithromycin.

In a further aspect, there is provided a composition comprising a combination of two or more antibiotic agents for the treatment of an autoimmune disease, said two or more antibiotic agents selected from clofazimine, clarithromycin and at least one antibiotic having bactericidal activity.

In another aspect, the present disclosure provides a method of treating an autoimmune disease in a patient comprising administering a composition including rifabutin, clarithromycin, and clofazimine to said patient.

In a further aspect there is a method of treating a patient suffering from an autoimmune disease, and having, or susceptible to, infection by a *Mycobacterium*, comprising administering to the patient a composition including rifabutin, clarithromycin, and clofazimine.

In another aspect, there is a method of treating a patient suffering from multiple sclerosis, said patient also testing positive for a mycobacterial infection comprising administering to the patient a composition including rifabutin, clarithromycin, and clofazimine.

In another aspect, the present disclosure provides a method of treating an auto-immune disease in a patient comprising administering a composition comprising a combination of antibiotics selected from the group rifabutin, clarithromycin, and clofazimine to said patient.

In another aspect, the present disclosure provides a method of treating multiple sclerosis in a patient comprising administering a composition comprising a combination of antibiotics selected from the group rifabutin, clarithromycin, and clofazimine to said patient.

DESCRIPTION OF EXEMPLARY EMBODIMENTS OF THE DISCLOSURE

Figure 1:
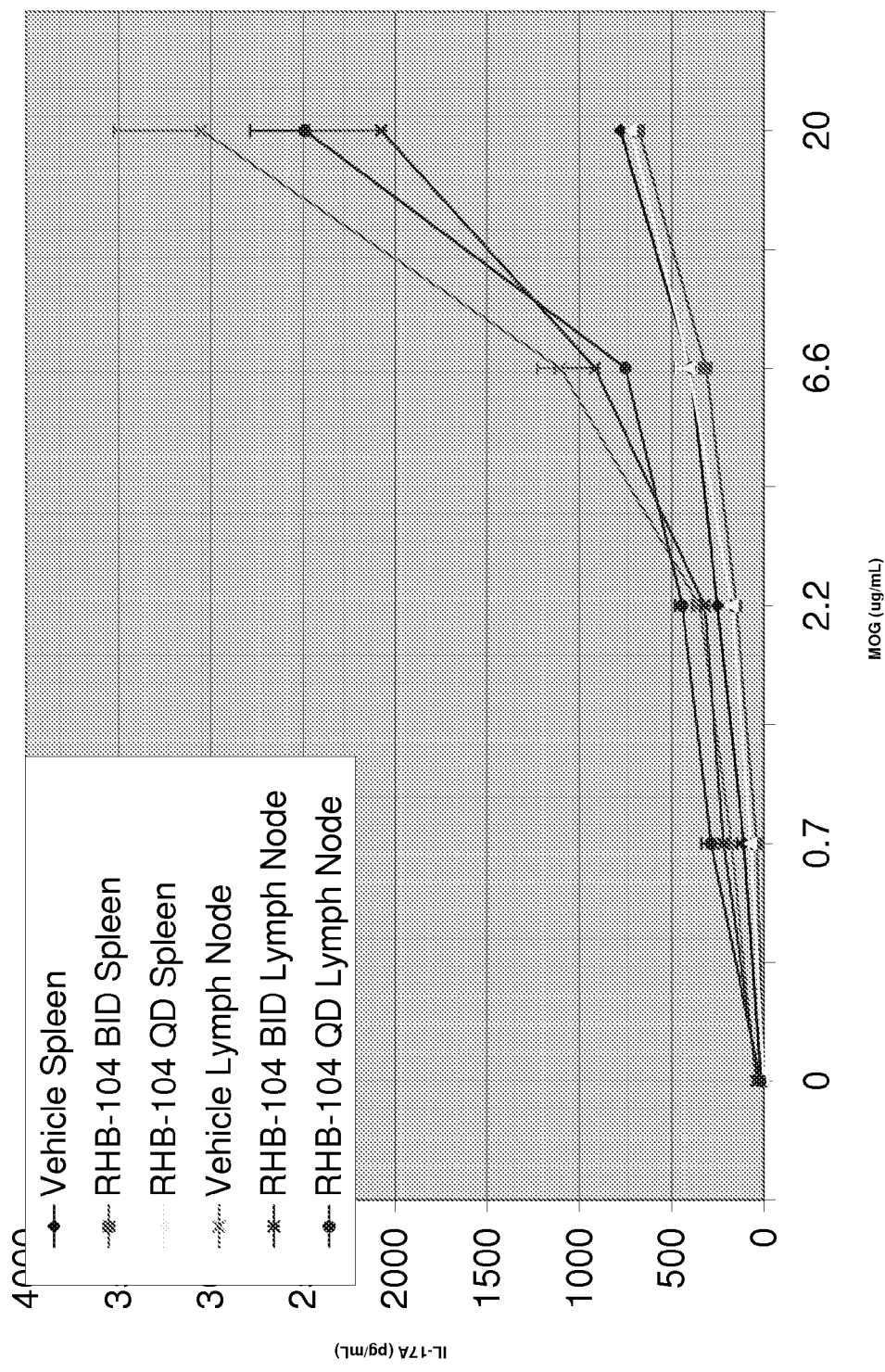
FIG. 1 is a graph showing the effects of administration of RHB 104 on the concentration of cytokine IL-17 in a mouse model.

By the term "multiple sclerosis", multiple sclerosis variants such as Neuromyelitis Optica (Devic's Disease), Diffuse Sclerosis, Transitional Sclerosis, Acute Disseminated Encephalomyelitis, and Optic Neuritis are also incorporated.

Use of the term "subject" includes both human and non-human animals.

"Treatment" is meant that at least an amelioration of the symptoms associated with the condition (eg MS) afflicting the subject is achieved, where amelioration is used in a broad sense to refer to at least a reduction in the magnitude of a parameter, e.g., symptom, associated with the condition being treated. As such, treatment also includes situations where the condition, or at least symptoms associated therewith, are completely inhibited, e.g., prevented from happening, or stopped, e.g. terminated, such that the subject no longer suffers from the condition, or at least the symptoms that characterize the condition. "Treatment" also includes the prevention of a relapse episode in a subject or should the relapse episode occur then the term "treatment" is as above.

A variety of subjects are treatable according to the subject methods. In many embodiments the subjects are "mammals" or "mammalian", where these terms are used broadly to describe organisms which are within the class mammalian, including the orders carnivore (e.g., dogs and cats), rodentia (e.g., mice, guinea pigs, and rats), and primates (e.g., humans, chimpanzees, and monkeys). In many embodiments, the subjects are humans. While the present invention may be used for the treatment of a human subject, it is to be understood that the subject methods may also be carried-out on other animal subjects such as, but not limited to, mice, rats, dogs, cats, livestock and horses, etc. Accordingly, it is to be understood that any subject in need of being treated according to the subject invention is suitable.

Moreover, suitable subjects of this invention include those who have and those who have not previously been afflicted with a condition, those that have previously been determined to be at risk of suffering from a condition, and those who have been initially diagnosed or identified as being afflicted with or experiencing a condition.

Treatment may be assessed using any one or more of a number of criteria. The assessment of said treatment may be either or both quantitative or qualititative. Assessment of treatment may be made based on a clinical scale of severity of a disease. In subjects being treated for an autoimmune disease such as MS, the treatment may be assessed using a number of scales such as the Expanded Disability Status (EDSS), the Ambulation Index (AI) or the Scripps Neurologic Rating Scale (SNRS).

Assessment of treatment may include the assessment of one or more symptoms associated with a particular disease.

In the example of MS, symptoms include: weakness and/or numbness in one or more limbs; tingling of the extremities and tight band-like sensations around the trunk or limbs; dragging or poor control of one or both legs to spastic or ataxic parepesis; hyperactive tendon reflexes; disappearance of abdominal reflexes; Lhermitte's sign; retrobulbar or optic neuritis; unsteadiness in walking; brain stem symptoms (diplopia, vertigo, vomiting); disorders of micturition; hemiplegia; trigeminal neuralgia; other pain syndromes; nystagmus and ataxia; cerebellar-type ataxia; Charcot's triad; diplopia; bilateral internuclear ophthalmoplegia; myokymia or paralysis of facial muscles; deafness; tinnitus; unformed auditory hallucinations; vertigo and vomiting; transient facial anesthesia or of trigeminal neuralgia; bladder dysfunction; euphoria; depression; dementia, dull, aching pain in the low back; sharp, burning, poorly localized pains in a limb or both legs and girdle pains; abrupt attacks of neurologic deficit; dysarthria and ataxia; paroxysmal pain and dysesthesia in a limb; flashing lights; paroxysmal itching; and/or tonic seizures, taking the form of flexion (dystonic) spasm of the hand, wrist, and elbow with extension of the lower limb.

In MS, ameliorating symptoms of the disease further include reducing the number of inflammatory episodes ("episode" includes any or a combination of at least the above clinical manifestations), slowing the progression of the disease, or reducing/slowing down the appearance of brain lesions (identified by magnetic resonance imaging). The recurrence of diseases including MS can be ameliorated by decreasing the severity of the symptoms (eg the symptoms described above) associated with an MS episode, or by lengthening the time period between the occurrence of episodes.

In MS and associated diseases, quantitative analysis may also be used to assess treatment. Examples of quantitative analysis techniques include the identification of biological markers. Examples include but are not limited to biomarkers which reflect alteration of the immune system; biomarkers of blood-brain barrier disruption, of demyelination, of oxidative states and excitotoxicity, of gliosis or of remyelination and repair. A panel of various markers may be measured to reflect various stages of disease including various stages of inflammation, demyelination, axonal degeneration and remyelination.

It is to be appreciated that the assessment of treatment may result from a number of techniques and may rely on both clinical manifestation and the analysis of various non-clinical markers such as biomarkers. In diseases such as MS which is a complex disease with several pathophysiological mechanisms which are not uniform in MS patient sub-groups, there is a need to assess treatments based on various and differing criteria and markers and it is to be understood that the above examples provided for the assessment of treatment is not an exhaustive list but merely provides example of the means by which treatment may be evaluated.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The composition of the present disclosure may further comprise at least one antibiotic active against Gram positive bacteria "Gram positive antibiotic". The Gram positive antibiotic may be selected from one or more of the group comprising daptomycin, clindamycin, rifampicin, erythromycin, oleandomycin, roxithromycin, azithromycin, kanamycin, gentamycin, tombramycin, streptomycin, neomycin, paromomycin, ethambutol, isoniazid, minocyclin, tetracycline.

The term "one or more" antibiotic agents includes but is not limited to one, two, three, four, five, six etc. antibiotic agents. It is to be understood that the skilled artisan is able to empirically determine the specific number of antibiotic agents needed for use according to the embodiments provided herein and as known in the art.

The present compositions may be used for treating a patient suffering from an auto-immune disease wherein said patient also tests positive for infection with the bacterium *Mycobacterium avium paratuberculosis* (MAP).

The auto-immune disease may be multiple sclerosis.

Still further, the autoimmune disease may be Hashimoto's Thyroiditis, Melkersson-Rosenthal syndrome, Sarcoidosis or other similar diseases.

In another embodiment, the term auto-immune disease includes any of a large group of diseases characterized by abnormal functioning of the immune system resulting in antibodies against self tissue.

The antibiotics or compositions presently disclosed may be administered orally. Alternatively, the antibiotics may be administered intravenously.

Other routes of administration are contemplated including, but not limited to, intramuscular and intraosseous routes.

Each antibiotic may be administered separately. Alternatively two or more antibiotics may be administered together.

In one embodiment, the compositions provided herein comprise at least two antibiotic agents that are co-formulated in a single dosage form. In another embodiment, the composition provided herein comprises at least three antibiotics that are co-formulated in a single dosage form.

In one embodiment, each of rifabutin, clarithromycin, and clofazimine are co-formulated into a single dosage form.

Alternatively, each antibiotic agent may be formulated in a dosage form separately to the other antibiotic agents. In this embodiment, it is envisaged that the separate dosage forms would be packaged together in a kit to ensure that each was taken at generally the same time by a patient. In another embodiment, two of the antibiotic agents may be formulated in a single first dosage form and the remaining antiobiotic agent(s) may be separately formulated in a second dosage form to be taken with the first dosage form.

In one embodiment the present antibiotics and compositions may be available in the form of a tablet containing at least one of rifabutin, clarithromycin, and clofazimine in a powdered form. In some instances two of or all three of rifabutin, clarithromycin, and clofazimine are in a powdered form. Alternatively, present compositions may be in the form of a tablet capsule containing at least one of rifabutin, clarithromycin, and clofazimine in a microencapsulated form. In one embodiment, two or all of rifabutin, clarithromycin, and clofazimine are in a microencapsulated form.

In a further embodiment, present compositions may be in the form of a tablet capsule containing at least one of rifabutin, clarithromycin, and clofazimine in a powdered form, and the remaining agents present in a microencapsulated form. As a further possibility, present compositions may be in the form of a tablet capsule containing one or more of rifabutin, clarithromycin, and clofazimine present in a microgranulated form. In additional embodiments, present compositions may be in the form of a tablet containing one or more of rifabutin, clarithromycin, and clofazimine within a capsule, a capsule containing one or more of rifabutin, clarithromycin, and clofazimine within a tablet, a capsule containing one or more of rifabutin, clarithromycin, and clofazimine within an outer capsule containing the other agents, or any combination of the above.

In a further embodiment, the present compositions comprise an inner capsule containing rifabutin, within an outer capsule containing clarithromycin and clofazimine, wherein clarithromycin and clofazimine may be present in powdered, microencapsulated, or microgranulated forms. Still further, the present compositions may comprise liposome-encapsulated, un-encapsulated or polymer-coated liposome-encapsulated forms.

The present methods may be carried out by administration of one or more tablets/capsules containing rifabutin, clarithromycin, and clofazimine as described above, or through the administration of each of these separately. In preferred embodiments, rifabutin, clarithromycin, and clofazimine are administered simultaneously in one dose.

The present compositions may be prepared by means known in the art for the preparation of pharmaceutical compositions including blending, grinding, homogenizing, suspending, dissolving, emulsifying, dispersing, and, where appropriate, mixing of rifabutin, clarithromycin, and clofazimine together with selected excipients, diluents, carriers and adjuvants.

For oral administration, the present compositions may be in the form of tablets, lozenges, pills, troches, capsules, elixirs, powders, including lyophilized powders, solutions, granules, suspensions, emulsions, syrups and tinctures. The present compositions may comprise slow-release, or delayed-release forms for example in the form of coated particles, multi-layer tablets or microgranules.

Solid forms of the present compositions for oral administration may contain pharmaceutically acceptable binders, sweeteners, disintegrating agents, diluents, flavorings, coating agents, preservatives, lubricants, and/or time delay agents. Suitable binders include gum acacia, gelatin, corn starch, gum tragacanth, sodium alginate, carboxymethylcellulose or polyethylene glycol (PEG). Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange, or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms of the present compositions for oral administration may contain, in addition to the above agents, a liquid carrier. Suitable liquid carriers include water, oils, such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, or mixtures thereof.

Suspensions of the present compositions for oral administration may further include dispersing agents and/or suspending agents. Suitable suspending agents include sodium carboxymethylcellulose, methylcellulose, hydroxypropylmethyl-cellulose, poly-vinyl-pyrrolidone, sodium alginate or ceryl alcohol. Suitable dispersing agents include lecithin, polyoxyethylene esters of fatty acids such as stearic acid, polyoxyethylene sorbitol mono- or dioleate, -stearate or -laurate, polyoxyethylene sorbitan mono- or -dioleate, -stearate or -laurate, and the like.

Emulsions of the present compositions for oral administration may further include one or more emulsifying agents. Suitable emulsifying agents include dispersing agents as exemplified above or natural gums such as gum acacia or gum tragacanth.

Each antibiotic may be administered daily. Alternatively, each antibiotic may be administered twice a day. In another embodiment, each antibiotic may be administered three times a day. In a further embodiment, each antibiotic may be administered from the following: every 3 hours, every 4 hours, every 5 hours, every 6 hours, every 7 hours, every 8 hours, every 9 hours, every 10 hours, every 11 hours or every 12 hours. The administration of said antibiotics may be for a period of 1 week, 2 weeks, 3 weeks, 4 weeks, 5 weeks, 6 weeks, 7 weeks, 8 weeks or greater. It should be appreciated that the treatment period may continue for 3 months, 4, months, 5 months, 6 months, 7 months, 8 months, 9 months, 10 months, 11 months or 1 year or more.

The dosage of clarithromycin may be from 250 mg to 1.5 g per day, more typically about 950 mg per day. Said 950 mg may be administered in 95 mg capsules, requiring ten capsules per day. The typical dosage of rifabutin is from 150 mg to 750 mg per day, more typically about 450 mg per day. The typical dosage of clofazimine is from 50 to 500 mg per day. Typically the dosage of clofazimine is around 100 mg/day. Said 100 mg may be administered in 10 mg capsules, ten times per day. The dosage of clofazimine may further be calculated by weight and maybe from about 1 mg/kg to about 6 mg/kg, more typically about 2 mg/kg.

In children, the following doses (in mg/day) are envisaged:

|  | Child Weight (kg) | |
| --- | --- | --- |
|  | 15-30 | 30-45 |
| Clarithromycin | 225-550 | 450-675 |
| Clofazimine | 50 | 75 |
| Rifabutin | 258 | 180 |

In a further embodiment, ramp-up dosing may be followed in children.
For example:

| Antibiotic | Number of Capsules | | | | | | | | | |
| --- | --- | --- | --- | --- | --- | --- | --- | --- | --- | --- |
| Clarithromycin | 95 | 190 | 285 | 380 | 475 | 570 | 665 | 760 | 855 | 950 |
| Clofazimine | 10 | 20 | 30 | 40 | 50 | 60 | 70 | 80 | 90 | 100 |
| Rifabutin | 45 | 90 | 135 | 180 | 225 | 270 | 315 | 360 | 405 | 450 |

Weight of child 15-29.9 kg
 Weeks 1, 2 & 3=1 capsule daily
 Weeks 4 & 5=1 capsule twice daily (BID)
 Weeks 6 & 7=3 capsule daily
 Weeks 8 onward=2 capsule twice daily (BID)
Weight of child 30-45 kg
 Weeks 1=1 cap daily
 Weeks 2 & 3=1 caps twice daily (BID)
 Weeks 4 & 5=3 caps daily
 Weeks 6 & 7=2 caps twice daily (BID)
 Weeks 8 onward=5 caps daily
Weight of child >45 kg
 Week 1=1 cap twice daily (BID)
 Weeks 2 & 3=2 caps twice daily (BID)
 Weeks 4 & 5=3 caps twice daily (BID)
 Weeks 6 & 7=4 caps twice daily (BID)
 Weeks 8 onward dose of 5 caps twice daily (BID).

At least one antibiotic may be co-formulated with an absorption enhancer that may improve bioavailability of said antibiotic. The amount of absorption enhancer may be between 300-700% w/w relative to the amount of antibiotic. In certain embodiments, the absorption enhancer is polyethylene glycol. In one example, the polyethylene glycol has an average molecular weight of between 200-20,000 (such as, between 1000-15000, 5000-12000, 7000-9000, or 7500-8500).

In a further embodiment, a method of formulating the present compositions includes dispersing at least said clofazimine in PEG to form a PEG/clofazimine dispersion and subsequently mixing said PEG/clofazimine dispersion with at least one of said other antibiotic agents. In one embodiment, the PEG/clofazimine dispersion is mixed with both clarithromycin and rifabutin. Similarly, the clarithromycin or the rifabutin may be first dispersed in PEG and subsequently mixed with the remaining antibiotics.

The present compositions may further include a vitamin. In a particular embodiment, the present compositions include Vitamin D.

The present compositions may further include an anti-inflammatory agent. The anti-inflammatory agent may include 5-aminosalicylic acid. Alternatively the anti-inflammatory may comprise Azathioprine. Another anti-inflammatory may comprise Methotrexate.

The present compositions may further comprise a cyclin dependent kinase inhibitor. An example includes R-roscovitine. A further example includes Flavopiridol.

Further, the present compositions may comprise an activated T-cell transcription inhibitor. An example includes Tacrolimus.

MS patients have been found to display immunological and cytokine elevations consistent with those found in chronic infections. The present disclosure relates to the use of immunomodulatory properties of antibiotics as one therapeutic approach for attenuating a host's inflammatory response, particularly in instances of autoimmune responses with a view to treating autoimmune diseases.

Bacteriolytic antibiotics such as β-lactams work by inhibiting bacterial cell wall synthesis, leading to lysis of the pathogen and, therefore, to the release of pro-inflammatory bacterial components which result in an increasing mortality and sequelae. Contrary to the above, bactericidal antibiotics such as rifabutin prevent the initial inflammatory burst. In vitro data suggest that therapy with non-bacteriolytic antibiotics causes less inflammation and could ameliorate the outcome of severe infections.

Macrolide antibiotics have a superior immunomodulatory action. Clarithromycin reduces the bacterial viability correlated with a decline in bacterial protein synthesis as shown by a time-dependent intracellular accumulation established in a number of bacterial infections. Macrolides such as clarithromycin inhibit synthesis of reactive oxygen species and/or secretion of pro-inflammatory cytokines in vitro while exerting variable effects on the release of anti-inflammatory cytokines.

The role of inflammatory cytokines in human inflammatory diseases was investigated and the effects of combination antibiotics on cytokine protein levels assessed.

As noted previously, multiple sclerosis is an autoimmune disease that involves the destruction of the myelin sheath that surrounds the neurons in the brain and spinal cord. It affects movement, sensation and bodily functions and is characterized by the infiltration of inflammatory cells in the CNS. Its etiology includes a combination of genetic and environmental factors. While its pathogenesis needs to be researched further, viral and/or microbial infections seem to contribute to the disease. It commonly affects young adults, women and Caucasians of Northern European ancestry.

In multiple sclerosis, major histocompatibility complex (MHC) class II proteins expressed on the surface of antigen presenting cells bind to myelin proteins or myelin related proteins, causing Th0 cells to undergo activation and differentiation. Th1 cells then cross the blood brain barrier into the CNS, engage antigen-MHC complexes and produce pro-inflammatory cytokines.

Experimental autoimmune encephalomyelitis (EAE) is the most commonly used mouse model of human multiple sclerosis (MS). Because of its many similarities to MS, EAE is used to study pathogenesis of autoimmunity, CNS inflammation, demyelination, cell trafficking and tolerance induction.

Recent research involving EAE animal models points to the role of a proinflammatory cascade of Th17 cells, IL-6 and TGF-β in the central nervous system in the pathogenesis of both EAE and MS. EAE shows clinical and pathological similarities to MS. The EAE model is central to the determination of therapeutic treatments (validity of the target, assessment of potential drug candidates, accelerated mode of study, analysis of histopathology).

Example 1: Cytokine Experiment

Mouse Model—Immunization with $MOG_{35-55}$/CFA

This study objective was to determine the effects of a composition comprising rifabutin, clarithromycin and clofazimine hereinafter referred to as formulation RHB 104 on the cytokine production by T lymphocytes from draining lymph nodes and spleen after immunization with $MOG_{35-55}$/CFA.

RHB-104 capsules comprise 10 mg clofazimine, 95 mg of clarithromycin and 45 mg of rifabutin and together with various excipients.

The embodiment of the composition used in this study and referred to as RHB 104 is provided below.

Composition of RHB-104 Capsules

| Ingredient (Grade) | Function | mg per capsule | % |
| --- | --- | --- | --- |
| Clofazimine (USP/Ph. Eur.). | Active | 10.00 | 3.23 |
| Rifabutin (USP/Ph. Eur.) | Active | 45.00 | 14.53 |
| Clarithromycin (USP/Ph. Eur.) | Active | 95.00 | 30.67 |
| Polyethylene Glycol 8000 (NF/Ph. Eur.) | Dispersing Agent | 50.00 | 16.14 |
| Polysorbate 80 (NF/Ph. Eur.) | Wetting Agent | 6.66 | 2.15 |
| Microcrystalline Cellulose 200 (NF/Ph. Eur.) | Diluent | 28.00 | 9.04 |
| Magnesium Stearate, vegetable grade (NF/Ph. Eur.) | Lubricant | 4.68 | 1.51 |
| Sodium Lauryl Sulfate (NF/Ph. Eur.) | Wetting Agent | 10.00 | 3.23 |
| Microcrystalline Cellulose 200 | Diluent | 60.42 | 19.51 |
| Hard Gelatin Capsule (Mfg. Std) | — | 1 unit | — |
| Total | | 309.76 | 100 |

Experimental Design

There were 3 experimental groups with 4 mice/group.

Disease was induced by immunizing mice on Day 0 with myelin oligodendrocyte glycoprotein, peptide 33-55 ($MOG_{35-55}$) emulsified in complete Freund's adjuvant (CFA) and treatment started on the same day. Eleven days after immunization, mice were euthanized, spleens and lymph nodes collected and cell suspensions prepared. Cell suspensions were cultured for 3 days in the presence of multiple concentrations of $MOG_{35-55}$. The culture supernatants were collected at the end of this 3-day culture period. The concentrations of 7 cytokines (IL-2, IL-4, IL-6, IL-10, IL-17A, TNF-alpha and IFN-γ) were determined in the culture supernatants using Th1/Th2/Th17 cytokine bead assay (CBA) kits from Becton Dickinson.

Mice and Immunization

The study used a total of 12 female C57BL/6 mice (Taconic Farms, 14 weeks old).

On Day 0, mice were immunized at two sites in the back s.c. with $MOG_{35-55}$/CFA.

Groups and Treatment

Treatment started on Day 0 (day of immunization) and continued until mice were sacrificed on Day 11.
Group 1—Vehicle, 10 mL/kg, p.o., BID (negative control)
Group 2—RHB-104, 36 mg/kg, p.o., BID, 10 mL/kg
Group 3—RHB-104, 36 mg/kg, p.o., QD, 10 mL/kg
    AM dosing: RHB-104, 36 mg/kg, p.o., QD, 10 mL/kg
    PM dosing: Vehicle, QD, 10 mL/kg (control for dosing stress)

All dosing was performed at the same time (+/−1 hour) each day. There was at least 10 hours between morning and evening dosing and not more than 14 hours between evening and morning dosing.

All mice were sacrificed 1 to 4 hours after the morning dose on Day 11.

Spleen and Lymph Node Cell Cultures

Spleens from all mice were collected, pooled for each group, and cell suspensions prepared.

Inguinal lymph nodes from all mice were collected, pooled for each group, and cell suspensions prepared.

From each cell suspension, cultures were set up in 96-well plates with five concentrations of $MOG_{35-55}$; none, 0.7, 2.2, 6.7, and 20.0 µg/mL, all in triplicates.

After 72 hours of culture, supernatants were collected.

Cytokine concentrations in each culture were measured using CBA Th1/Th2/Th17 kit (Mouse Th1/Th2/Th17 BD™ Cytometric Bead Array (CBA) kit, Becton Dickinson). This kit allows simultaneous measurement of 7 different cytokine concentrations (IL-10, IL-4, IL-2, IL-17A, IFN-γ, TNF-alpha, IL-6).

Results

1) Cytokine IL-10

IL-10 was below standard range, so any changes could not be observed.

2) Cytokine IL-17 A

Dosing with RHB-104 BID demonstrated a reduction in the cytokine levels in the lymph nodes and to a lesser extent in the spleen as seen in FIG. 1.

3) Cytokine TNF-Alpha

Figure 2:
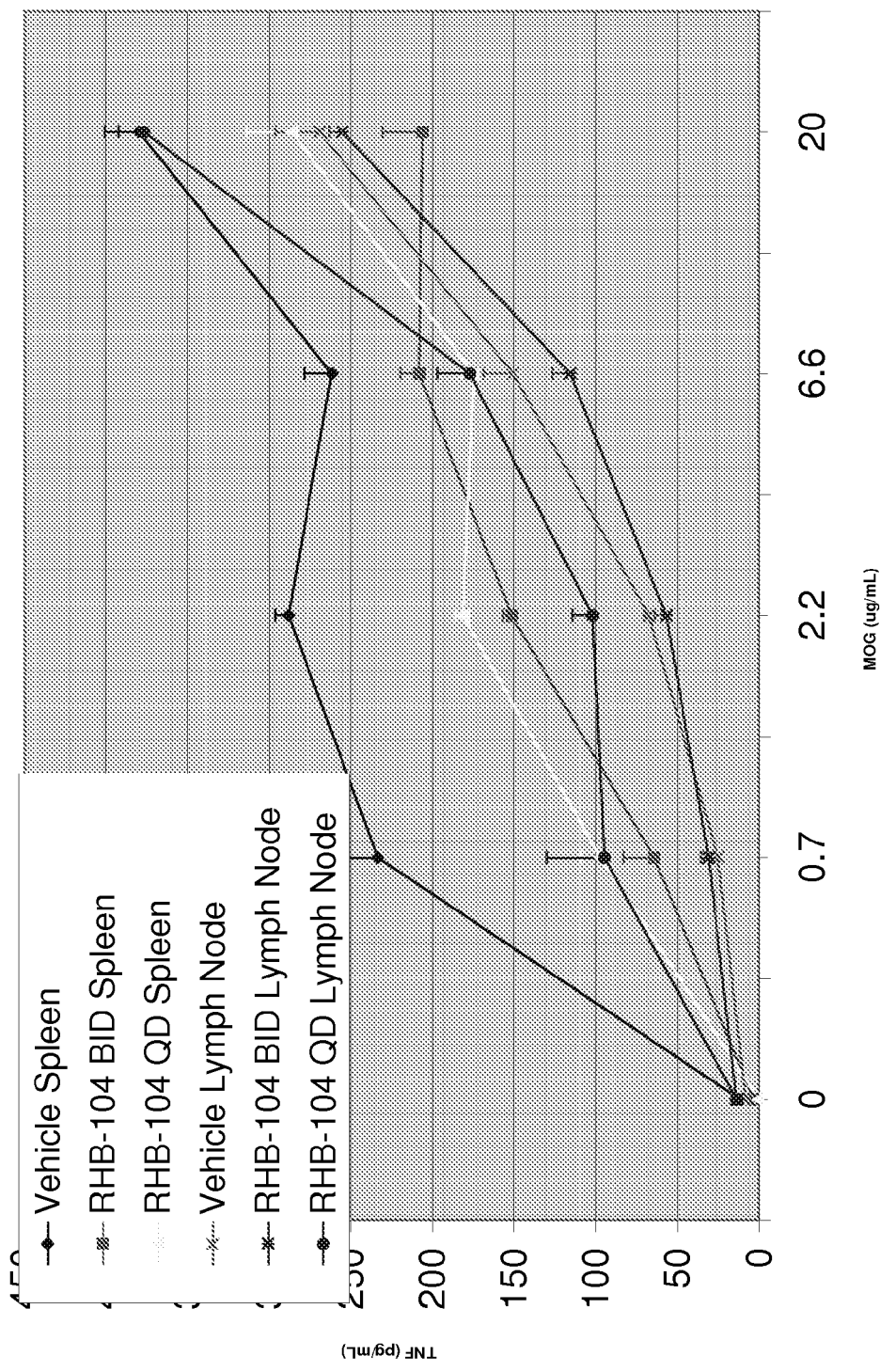
FIG. 2 is a graph showing the effects of administration of RHB 104 on the concentration of cytokine TNF-alpha in a mouse model.

RHB-104 BID and QD dosing reduced TNF-alpha in the spleen. Additionally, BID dosing reduced TN-alpha in the lymph nodes. BID dosing reduction of the TNF-alpha in the spleen was almost 50% as shown in FIG. 2.

4) Cytokine IFN-gamma

Figure 3:
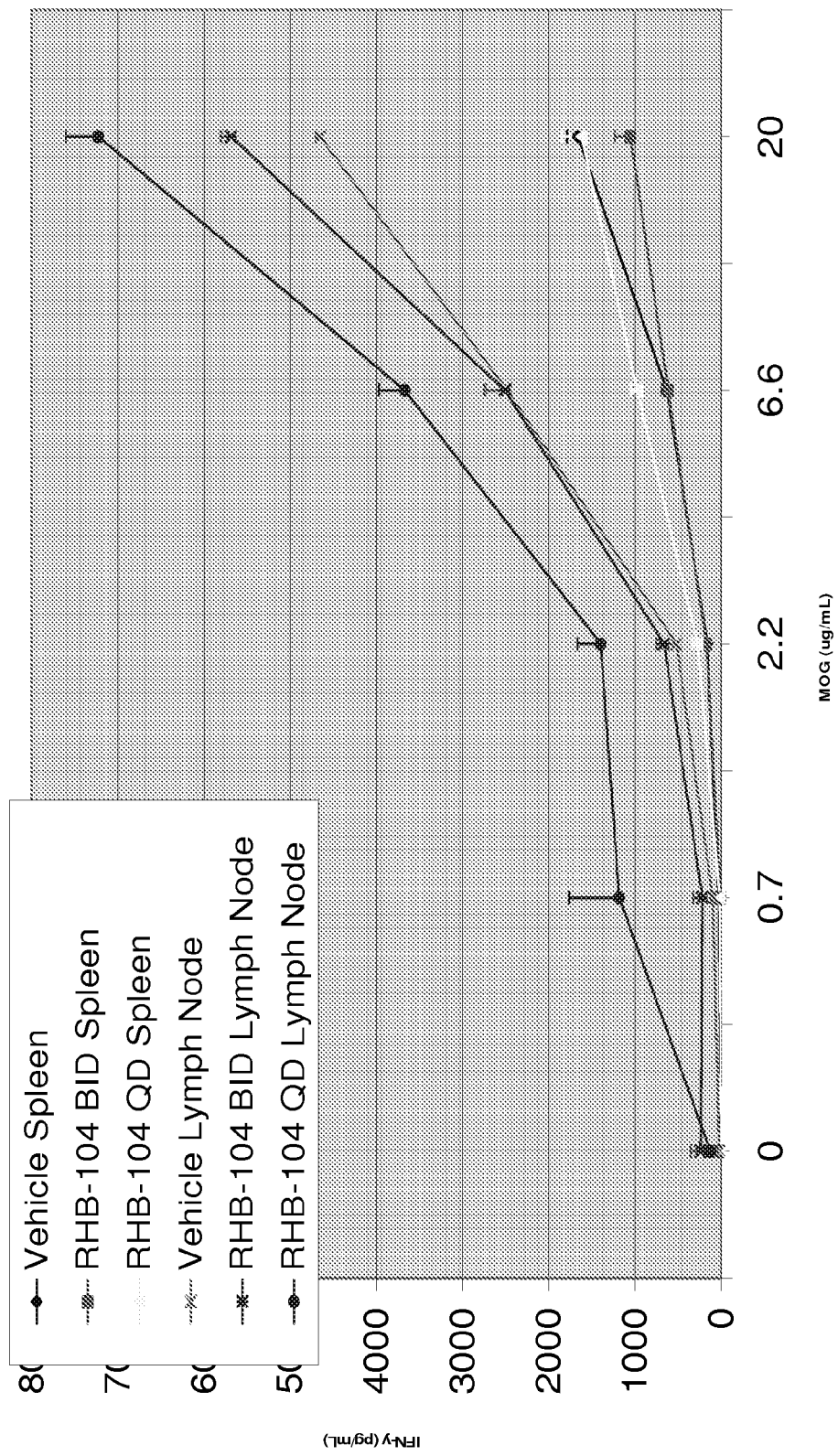
FIG. 3 is a graph showing the effects of administration of RHB 104 on the concentration of cytokine IFN-gamma in a mouse model.

RHB-104 reduced IFN-gamma for BID dosing in the spleen as shown in FIG. 3:

5) Cytokine IL-6

Figure 4:
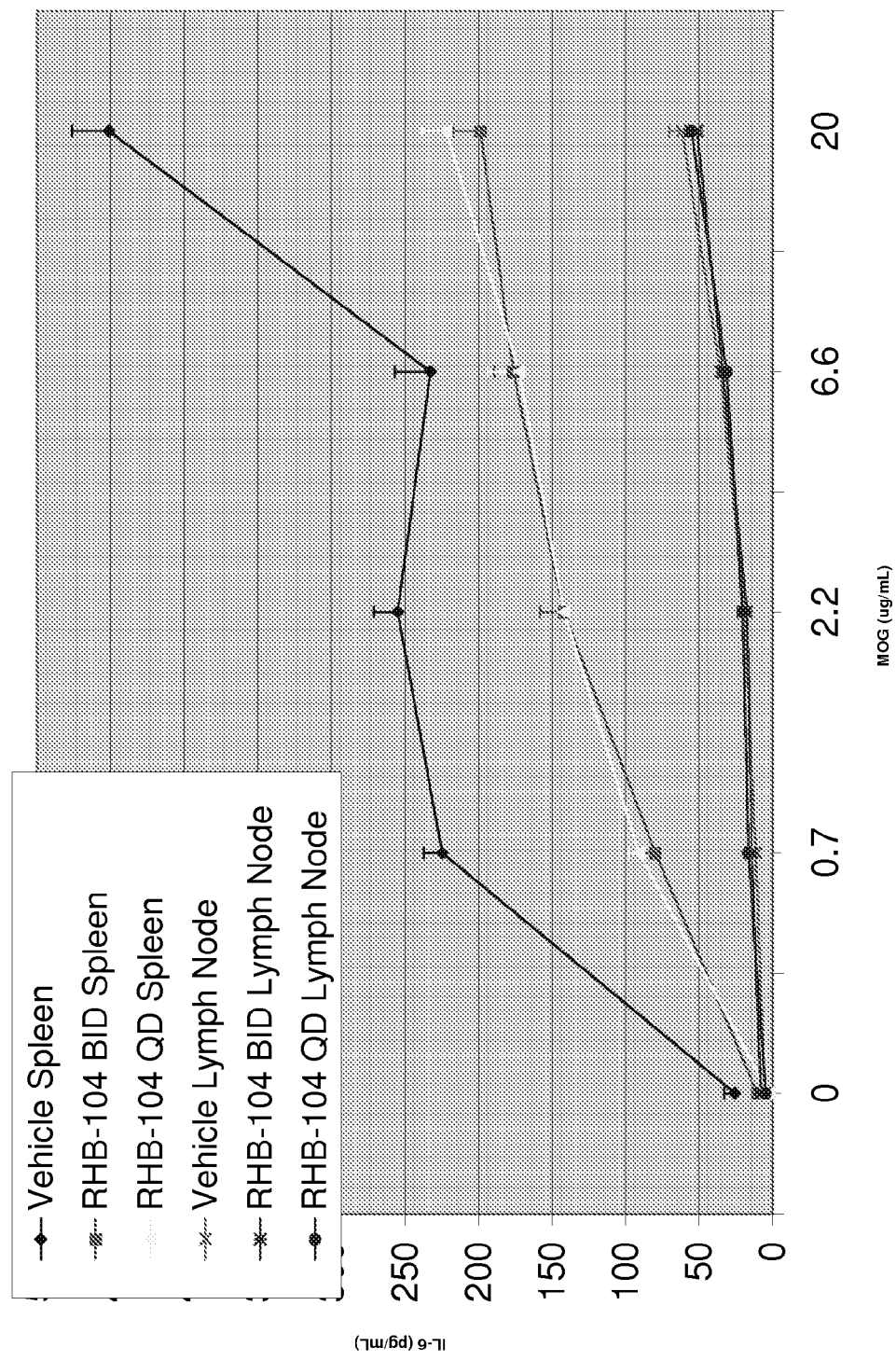
FIG. 4 is a graph showing the effects of administration of RHB 104 on the concentration of cytokine IL-6 in a mouse model.

RHB 104 BID dosing in the spleen showed an almost 50% reduction of IL-6 in the spleen as shown in FIG. 4.

6) Cytokine IL-4

IL-4 was below standard detection.

7) Cytokine IL-2

Figure 5:
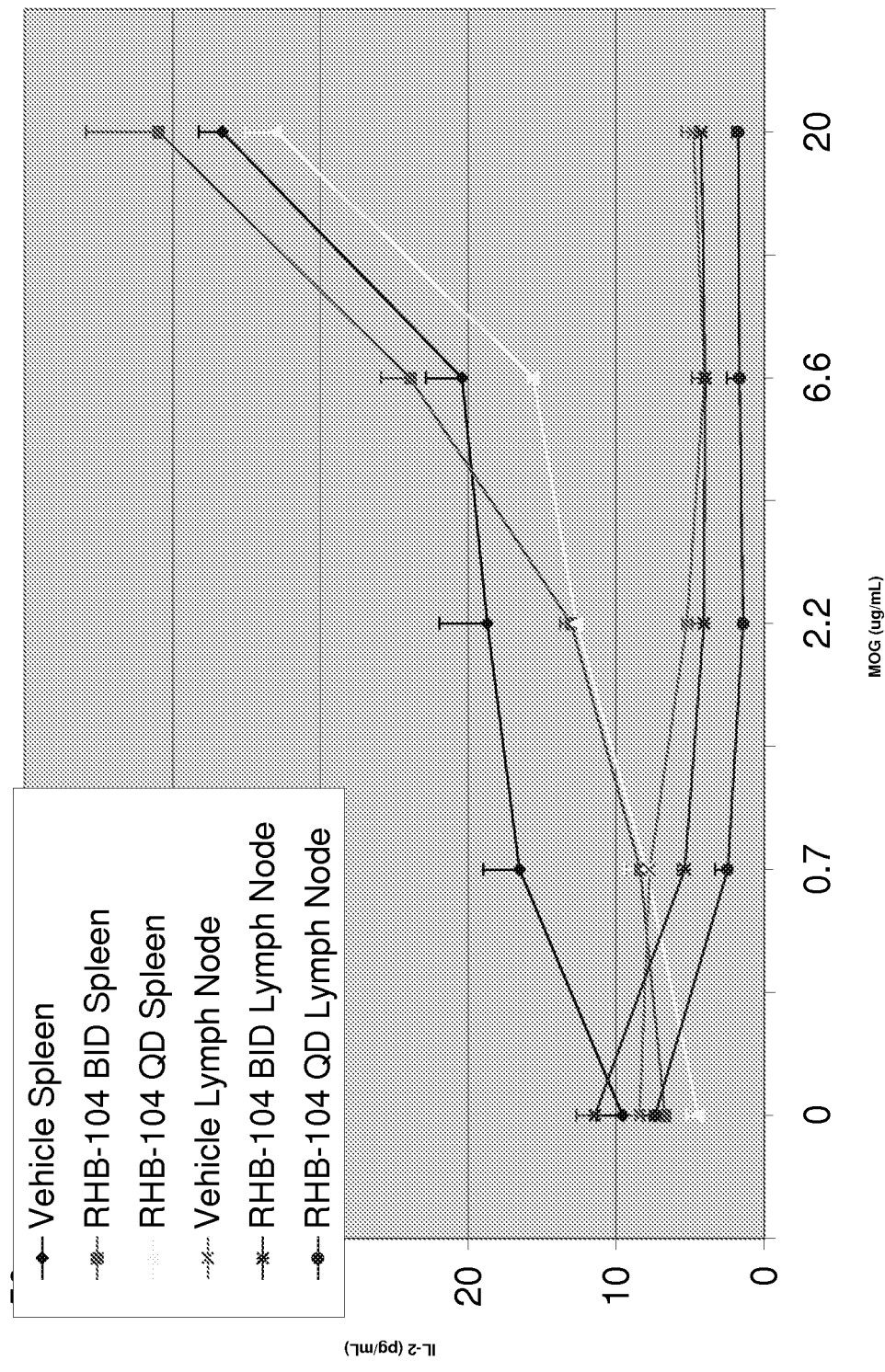
FIG. 5 is a graph showing the effects of administration of RHB 104 on the concentration of cytokine IL-2 in a mouse model.

RHB-104 reduced IL-2 in QD dosing in both spleen and lymph nodes as shown in FIG. 5.

The effect of the formulation RHB 104 comprising rifabutin, clarithromycin and clofazimine on cytokine levels in the above mouse model supported further analysis in an EAE mouse model which is a well recognised model for human MS:

Experiment 2

Evaluation of the Efficacy of RHB 104 Administered in a Mouse Model of EAE

Background and Overview of EAE Model

EAE Induction

Chronic EAE develops in C57BL/6 mice after immunization with an emulsion of $MOG_{35-55}$CFA or $MOG_{1-125}$/CFA followed by injection of pertussis toxin. This model is used to test the potential of compounds to prevent or mitigate EAE disease. It can be run with the compound dosed from the time of immunization (prophylactic treatment), or with the aim of reversing the course of disease and facilitating recovery by dosing the compound from the time of EAE onset (therapeutic treatment).

The model uses female C57BL/6 mice of age 10 to 14 weeks at the start of the study. Typically, EAE develops 8-18 days after immunization. EAE development is usually followed for 4 weeks (28 days) after immunization.

Stress reduces mouse susceptibility to EAE. Aside from any compound effects, the administration of treatment during the disease induction period (~0-10 days after immunization) postpones disease onset and reduces disease severity. This is due to the stress of compound administration and the effects of the vehicle on the mice. The more frequent the administration and the less tolerated the vehicle, the greater the impact on disease development.

The stress of treatment and administration of vehicle has much less effect on disease development after clinical signs of EAE have appeared.

Prophylactic Treatment

In prophylactic studies, treatment begins before disease onset, at the time of immunization and group assignment. Mice are assigned to treatment groups in a balanced manner to achieve groups with similar distributions of body weights.

Prophylactic studies assess if treatment will affect the course of disease both before and after the first clinical signs of EAE.

To compensate for the stress of treatment in prophylactic treatment studies and achieve the target disease severity, EAE is induced with a higher dose of pertussis toxin than used in therapeutic studies. The dose of pertussis toxin is based on the expected stress due to dosing (route, frequency, and formulation of vehicle).

In prophylactic studies, median time to disease onset is usually the most sensitive measure of compound efficacy.

Small changes in the immune response can result in postponed disease onset—suppression of T cell activation and proliferation, antigen presentation, differentiation into Th1 and/or Th17 cells will all result in postponed onset of EAE.

Delayed onset of EAE accompanied with lower maximum severity indicates overall efficacy of treatment compared to the negative control group.

Therapeutic Treatment

In therapeutic treatment studies, treatment begins at the time of EAE onset. Mice are distributed into different treatment groups as they develop EAE (rolling enrolment) in a balanced manner to achieve groups with similar time of EAE onset and similar onset scores.

Therapeutic studies assess if treatment will reverse the course of disease or improve recovery from EAE.

The most important readout in this model is the average end clinical EAE score. This is the clinical outcome of the experiment; a reduction compared to the negative control group indicates treatment efficacy.

Course of EAE Development in Untreated Mice

Individual mice will have differing courses of disease. Most mice show initial signs of EAE between 9 and 14 days after immunization. Once EAE starts, the peak of disease almost always occurs 3-4 days later. The maximum score continues for several days and then mice partially recover. In some mice, disease will stay at maximum severity until the end of the study. Less often, a mouse will stay at the peak severity for only one day and then start recovering.

The extent of recovery largely depends on the maximum severity reached by the mouse. Most untreated or vehicle-treated mice will not fully recover, but their end score will usually be 0.5 to 1.5 points lower than their maximum score. About 25% of untreated or vehicle-treated mice show worsening EAE between 24 and 28 days after immunization, resembling a relapse. Spinal cords of these mice at the time of EAE worsening have a large number of inflammatory foci (≥7 foci per section), similar to histological findings at the time of EAE onset and peak, suggesting that these are true relapses with a new wave of inflammation in the spinal cords.

When mice are followed for a longer period of time, disease slowly increases in severity, resembling the chronic progressive course of disease observed in human MS patients.

During the course of EAE, changes in body weight reflect disease severity. Mice often lose a small amount of weight on the day following immunization. This appears to be due to effects of the administered adjuvant and pertussis toxin. Mice then steadily increase their body weight until disease onset. On the day of EAE onset, mice consistently lose 1-2 g of their body weight (5-10% of body weight). The weight loss continues with the progression of EAE severity, with the loss reaching around 20% of their pre-onset body weight at the peak of disease. The weight loss is most likely due to both paralysis and reduced food intake as well as high production of pro-inflammatory cytokines such as TNF during the acute phase of inflammation. After the peak of disease is reached, mice slowly gain weight, even if their clinical score does not improve. This increase in weight may be due to down regulation of inflammation which results in lower levels of pro-inflammatory cytokines in blood. Untreated or vehicle-treated mice usually have around 90% of their pre-immunization body weight 28 days after immunization.

Histology

Inflammation in EAE normally starts in the lumbar region of the spinal cord, spreading to the entire spinal cord by the peak of disease.

At onset of disease the number of inflammatory foci correlates strongly with disease severity. The number of foci increases until the peak of disease, when 6-15 inflammatory foci/section are typically found throughout the spinal cord. In the chronic stage of EAE (starting several days after the peak of disease), many inflammatory foci resolve, typically resulting in 3-4 inflammatory foci in each spinal cord section by approximately 28 days after immunization.

Because the largest numbers of inflammatory foci are present early in the course of disease, if histological analysis is performed at the end of the study, mice which have late EAE onset often have more inflammatory foci in their spinal cords than might be expected from their clinical score. For example, in a 28 day study a mouse with EAE onset on 27 days after immunization and an end clinical score of 2 will likely have more inflammatory foci than a mouse with EAE onset 9 days after immunization and an end score of 3.5. Similarly, a mouse which relapses shortly before the end of the study (relapse is defined as 1 or more points of increase in clinical score) will usually have more inflammatory foci at the end of the study than a mouse with stable chronic disease, even if the two have the same clinical score at the end of the study.

Demyelination is usually not found during the first two days after disease onset, but is found at the peak of disease (4-5 days after EAE onset) and continues during the chronic phase of EAE. Demyelination scores do not change much between the peak and 28 days after immunization and usually average between 1.2 and 2.5.

Demyelination is scored in both Luxol fast blue stained sections (LFB) and in H&E sections.

In LFB sections, spinal cord white matter stains dark blue and demyelinated areas are a lighter blue colour, and are associated with large vacuoles.

In H&E stained sections disruption of normal structure with large vacuoles is indicative of demyelination.

Apoptotic cells are identified in H&E sections, and are usually not found during the first two days of disease development. They are found at the peak and during the chronic stage of EAE. The average number of apoptotic cells is usually between 2 and 4 per section.

Experimental Design

Mice were weighed before the start of the study and then assigned to groups in a balanced manner. Compound treatment started on the day of immunization (Day 0 of the study).

Disease was induced by immunizing mice on Day 0 with myelin oligodendrocyte glycoprotein, peptide 35-55 ($MOG_{35-55}$) emulsified in complete Freund's adjuvant (CFA), followed by two injections of pertussis toxin (administered on Days 0 and 1).

To assess disease development, mice were weighed three times per week (Monday, Wednesday and Friday) from the time of immunization and scored daily for clinical signs of EAE starting on Day 7.

Materials and Methods

Mice

The study used a total of 24 female C57BL/6 mice (Taconic Farms, 10 weeks old).

Groups and Treatment

Mice were assigned to groups in a balanced manner to achieve similar weight at the start of the study.

Table 1 below shows which treatment was administered to each group.

TABLE 1

| Immunization and treatment regimen | | | | |
|---|---|---|---|---|
| Group | Compound | Dose | Frequency | Purpose |
| 1 | Vehicle | — | BID | Negative control |
| 2 | RHB-104 | 36 mg/kg | BID | Test compound |

Each group consisted of 12 mice.

Treatment of all groups was p.o., BID at a volume of 10 mL/kg.

Treatment started on the day of immunization (Day 0) and lasted until Day 27 after immunization. All dosing was performed at the same time (+/−1 hour) each day. There were no more than 14 hours between the evening and morning dose and no less than 10 hours between the morning and evening dose.

EAE Induction

EAE was induced in 24 female C57BL/6 mice (10 weeks old) as follows:

Day 0, Hour 0—Immunization with $MOG_{35-55}$/CFA

Day 0, Hour 2—Injection of pertussis toxin

Day 1, Hour 0—$2^{nd}$ injection of pertussis toxin (24 hours after initial immunization)

Mice were injected subcutaneously at two sites in the back with the modified emulsion component of the kit (containing $MOG_{35-55}$). One site of injection was in the area of upper back, approximately 1 cm caudal of the neck line. The second site was in the area of lower back, approximately 2 cm cranial of the base of the tail. The injection volume was 0.1 mL at each site.

Within 2 hours of the injection of emulsion, and then again 24 hours after the injection of emulsion, the pertussis toxin component of the kit was administered intraperitoneally. The volume of each injection was 0.1 mL.

Scoring and Readout

Readouts were EAE scores and body weight at the end of the study.

Mice were scored daily from Day 7 until the end of the study, and body weight was measured three times/week (Monday, Wednesday and Friday), starting on Day −1.

The last day of scoring was Day 28 after immunization.

Scoring was performed blind, by a person unaware of both treatment and of previous scores for each mouse.

EAE Scoring
EAE was scored on scale 0 to 5:
Score of 0.
  No obvious changes in motor functions of the mouse in comparison to non-immunized mice.
  When picked up by the tail, the tail has tension and is erect. Hind legs are usually spread apart.
  When the mouse is walking, there is no gait or head tilting.
Score of 1.
  Limp tail.
  When the mouse is picked up by the tail, instead of being erect, the whole tail drapes over finger.
Score of 2.
  Limp tail and weakness of hind legs.
  When mouse is picked up by tail, legs are not spread apart, but held closer together. When the mouse is observed walking, it has a clearly apparent wobbly walk.
Score of 3.
  Limp tail and complete paralysis of hind legs (most common); or
  Limp tail with paralysis of one front and one hind leg; or
  ALL of:
  Severe head tilting,
  Walking only along the edges of the cage,
  Pushing against the cage wall,
  Spinning when picked up by the tail.
Score of 4.
  Limp tail, complete hind leg and partial front leg paralysis.
  Mouse is minimally moving around the cage but appears alert and feeding.
  Usually, euthanasia is recommended after the mouse scores level 4 for 2 days. When the mouse is euthanized because of severe paralysis, score of 5 would be entered for that mouse for the rest of the experiment.
Score of 5.
  Complete hind and complete front leg paralysis, no movement around the cage; or
  Mouse is spontaneously rolling in the cage; or
  Mouse is found dead due to paralysis.
  In-between scores were assigned when the clinical signs fell between two above defined scores.
Histological Analysis of Spinal Cords
  On Day 28 (end of the study) all mice were sacrificed for histological analysis.
  Mice were perfused with PBS and spines were collected in 10% buffered formalin.
  For each mouse, 3 Luxol fast blue stained sections and 3 H&E sections, from lumbar, thoracic, and cervical spinal cord, were prepared and analysed.
  The histological analysis was performed by a pathologist blinded to the experimental groups and all clinical readouts.

Estimation of Demyelinated Area
  The demyelination score represents an estimate of demyelinated area for each section as follows:
  0—no demyelination (less than 5% demyelinated area)
  1—5 to 20% demyelinated area
  2—20 to 40% demyelinated area
  3—40 to 60% demyelinated area
  4—60 to 80% demyelinated area
  5—80 to 100% demyelinated area
  For Luxol fast blue stained slides, the size of the demyelinated area was estimated based on less intense blue staining of myelin.
  For H&E stained sections, the demyelinated area was estimated by looking for interruption of normal structure—pallor and vacuolation consistent with edema and demyelination, and dilated axons.
Count of Apoptotic Cells
  The number of apoptotic cells in each of the three H&E sections was determined. The apoptotic cells are neurons and their number correlates with disease stages. Apoptotic cells appear soon after disease onset, so at EAE onset there will be many inflammatory foci, but few apoptotic cells. Then, the number of apoptotic cells increases until the peak of disease, then remains elevated.
Statistical Analysis
  Statistical analysis was performed as follows:
  Disease incidence compared using Chi-square test
  Median day of EAE onset compared using Wilcoxon's survival test
  Mean day of EAE onset compared using two-tailed Student's t-test
  Mean maximum score (MMS) compared using Wilcoxon rank sum test
  End score compared using Wilcoxon rank sum test
  Change in body weight compared using two-tailed Student's t-test
  Demyelination scores (LFB) compared using Wilcoxon's non-parametric test
  Demyelination scores (H&E) compared using Wilcoxon's non-parametric test
  Number of apoptotic cells compared using 2-tailed Student's t-test
Results and Interpretation of Data
  EAE development was evaluated by comparing:
    EAE incidence,
    median and mean of day of EAE onset (MME),
    mean maximum score (MMS),
    average EAE scores at the end of the study, and
    average body weight at the end of the study relative to initial weight
  between the vehicle group (negative control) and the RHB-104 group
Summary of Results—Clinical Findings

TABLE 2

| Treatment | EAE incidence (%) | p value | MME | p value | MMS +/− SD | p value | End score +/− SD | p value | End % body weight +/− SD | p value |
|---|---|---|---|---|---|---|---|---|---|---|
| Vehicle | 100.0% |  | 15.0 |  | 3.08 +/− 0.87 |  | 2.54 +/− 1.05 |  | 90.7 +/− 7.5 |  |
| RHB-104 | 100.0% | 1.0000 | 15.0 | 0.7617 | 2.33 +/− 0.65 | 0.0031 | 0.92 +/− 0.67 | 0.0011 | 105.2 +/− 3.8 | 0.0000 |

Count of Inflammatory Foci
  Inflammatory foci of approximately 20 cells were counted in each H&E stained section. When inflammatory infiltrates consisted of more than 20 cells, an estimate was made of how many foci of 20 cells were present.

Group 1: Vehicle Group, p.o., BID (Negative Control)
  Most mice in this group developed severe EAE (Table 1 and FIG. 6).
  Most mice in this group lost weight during this study, which was expected (Table 1 and FIG. 7).

No mice died in this group.

Group 2: RHB-104, 36 mg/kg, p.o., BID

Most mice in this group developed milder disease than observed in the vehicle group.

Figure 6:
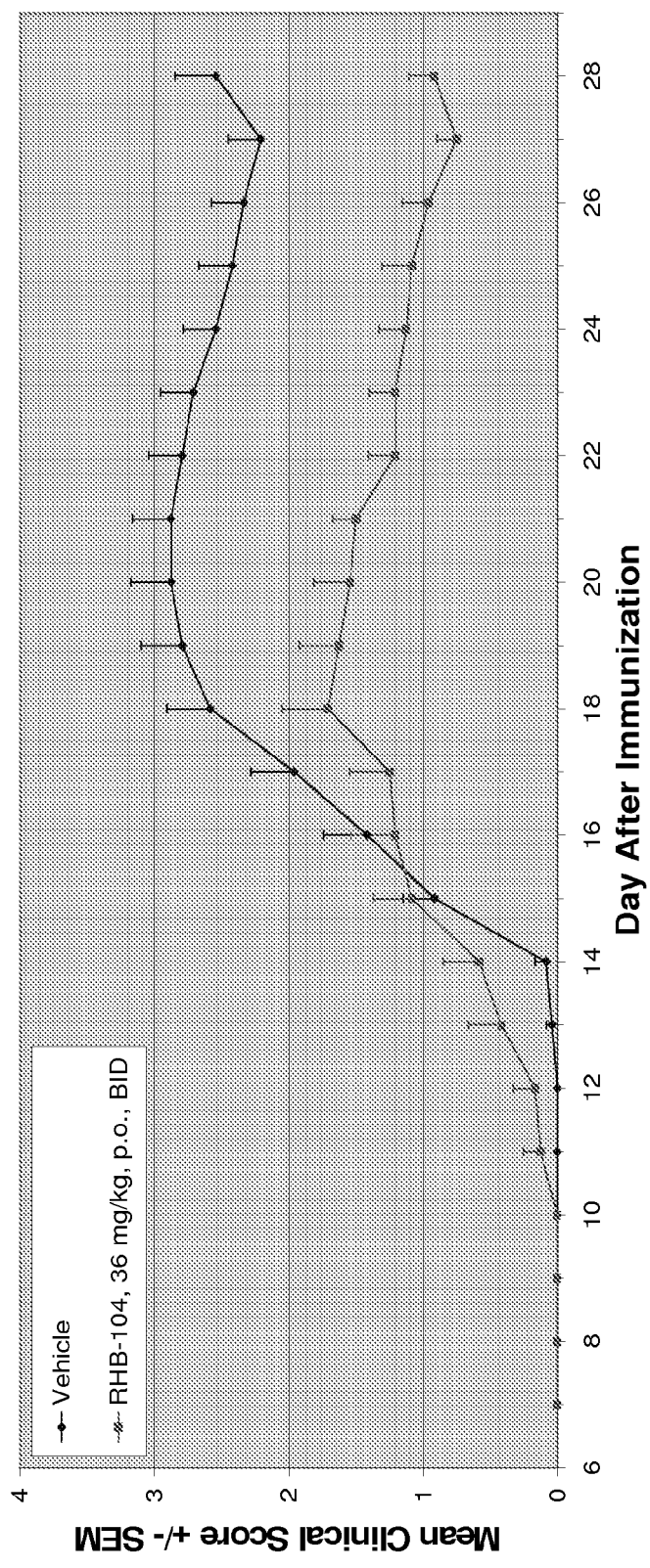
FIG. 6 is a graph showing EAE severity in various treatment groups in a recognised MS mouse model.
Figure 7:
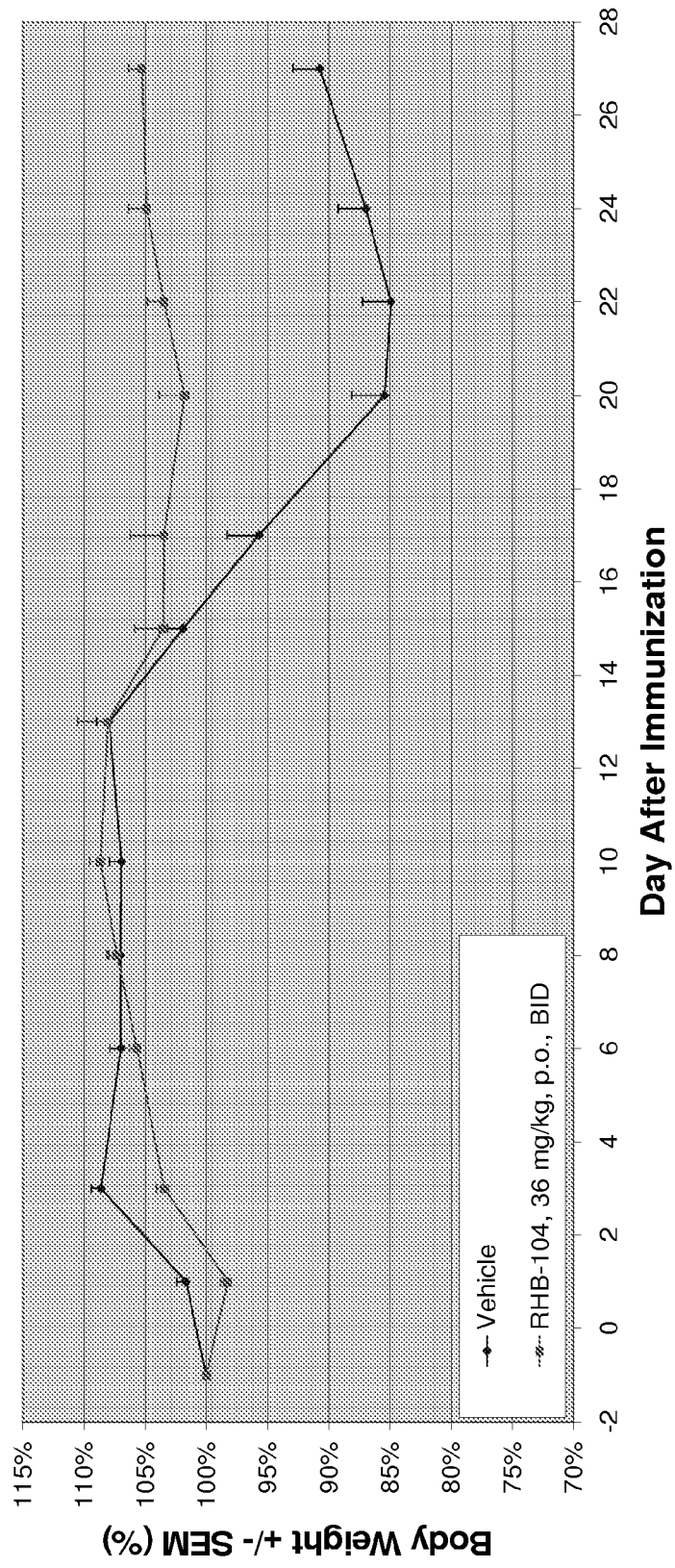
FIG. 7 is a graph showing the change in body weight in various treatment groups in a recognised MS mouse model.

This group was significantly improved in most clinical readouts of EAE compared to the vehicle group (Table 1 and FIGS. 6 and 7).

No mice died in this group.

The above results observed show a marked effect in relation to the severity of the disease by the abovementioned indicators upon treatment with RHB 104 when compared to a control in the recognised human MS mouse model.

Summary of Results—Histological Findings

TABLE 3

| Treatment | Inflammatory foci +/− SD | p value | Demyelination (LFB) +/− SD | p value | Demyelination (H&E) +/− SD | p value | Apoptotic cells +/− SD | p value |
|---|---|---|---|---|---|---|---|---|
| Vehicle | 3.2 +/− 2.2 | | 1.7 +/− 0.7 | | 1.4 +/− 0.6 | | 3.1 +/− 1.2 | |
| RHB-104 | 1.8 +/− 1.6 | 0.0867 | 0.6 +/− 0.6 | 0.0018 | 0.8 +/− 0.5 | 0.0198 | 1.4 +/− 1.7 | 0.0093 |

Vehicle Treated Mice

Histological findings in the vehicle-treated mice were typical for this stage and severity of EAE. Low magnification images of representative thoracic and lumbar spinal cord sections from vehicle treated mice showed that inflammation was present in the leptomeninges and in the white matter. No mice died in this group.

RHB 014 Treated Mice

Consistent with the clinical findings, most histological readouts in these mice were indicative of significantly less severe disease than in the vehicle-treated mice. Low magnification images of representative thoracic and lumbar spinal cord sections from RHB-104 treated mice showed fewer inflammatory foci in these sections than in sections from vehicle treated mice. In addition, the inflammatory foci were smaller in the RHB-104 treated mice than in vehicle treated mice.

Demyelinated areas were significantly smaller in the RHB-104 treated mice than in vehicle treated mice. No mice died in this group.

Figure 8:
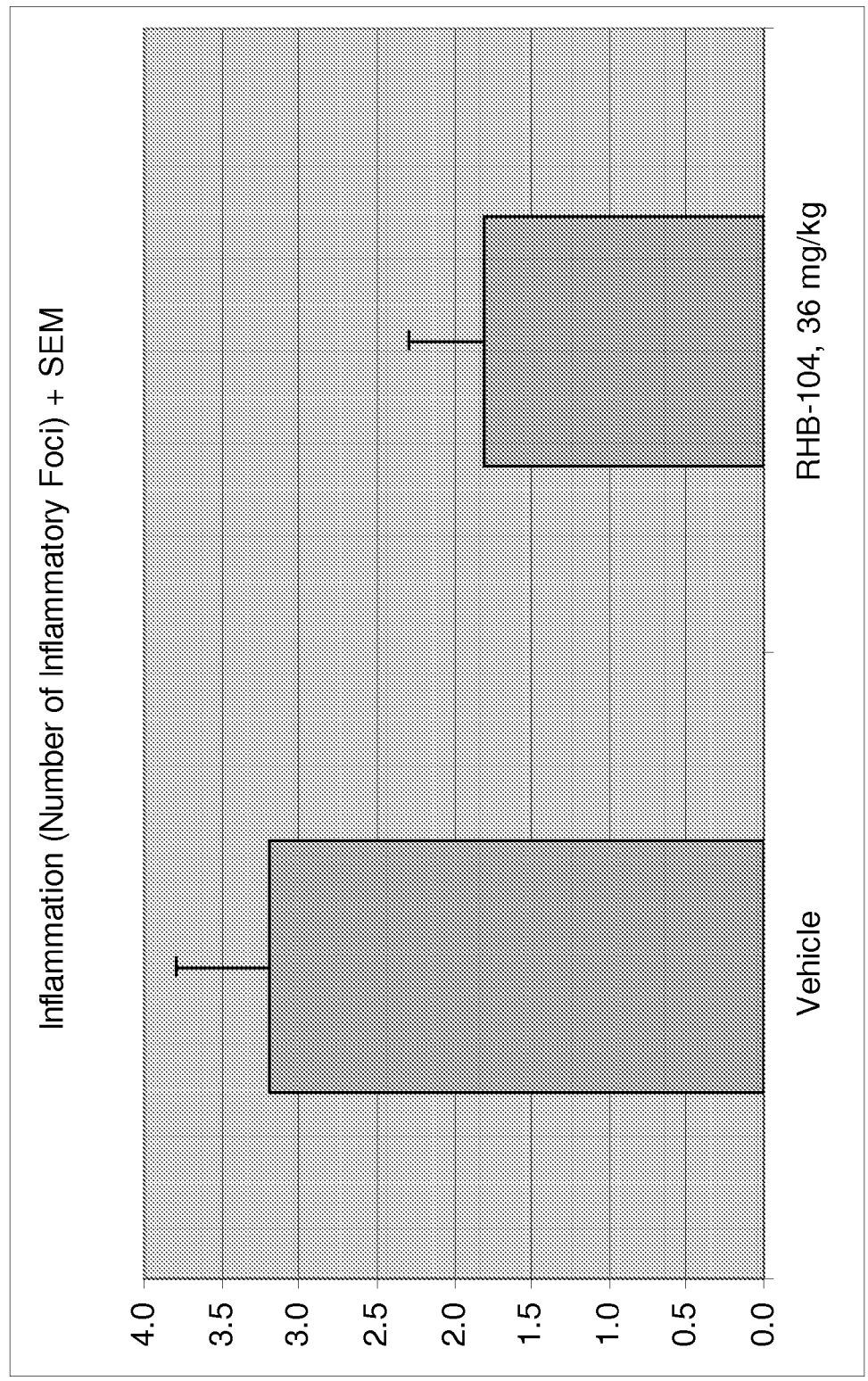
FIG. 8 is a graph showing the average number of inflammatory foci detected histologically (in H&E sections) in both a control and treatment group in a recognised MS mouse model.
Figure 9:
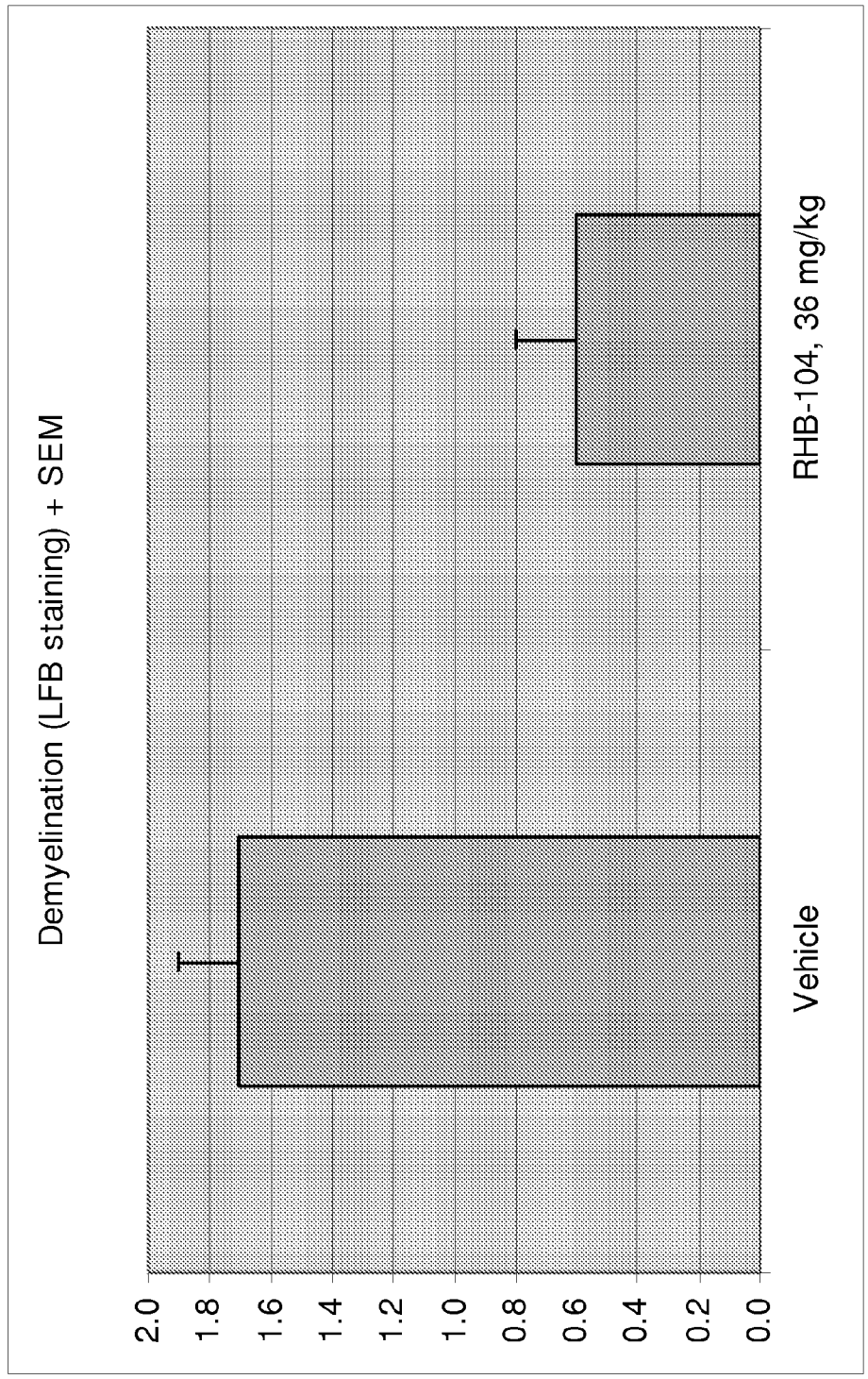
FIG. 9 is Graph 9 is a graph showing the average demyelination score from a histological analysis (from Luxol fast blue sections) in both a control and treatment group in a recognised MS mouse model.
Figure 10:
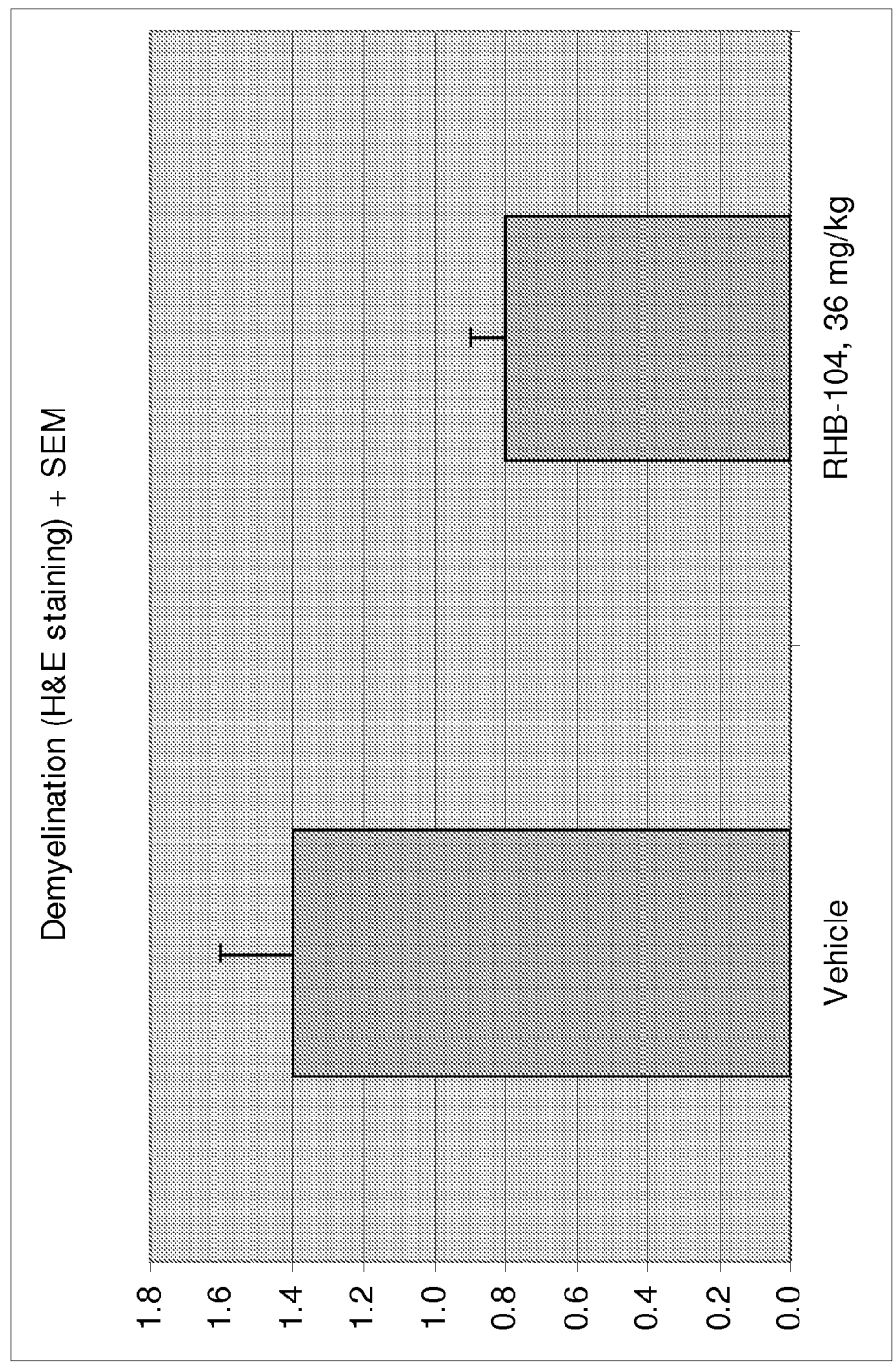
FIG. 10 is a graph showing the average demyelination score determined histologically (from H&E sections) in both a control and treatment group in a recognised MS mouse model.
Figure 11:
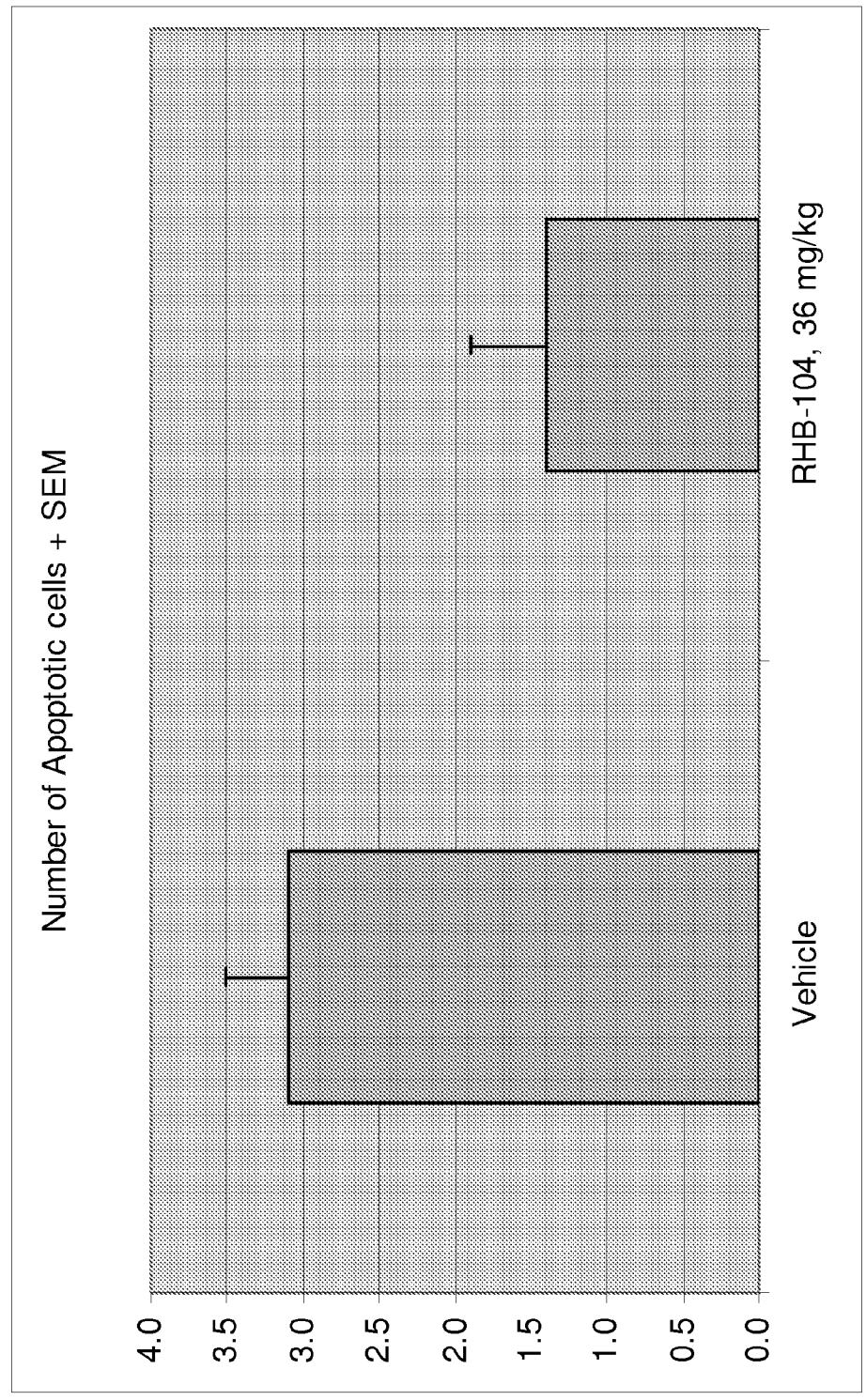
FIG. 11 is a graph showing the average number of apoptotic cells detected histologically (in H&E sections) in both a control and treatment group in a recognised MS mouse model.

The average number of inflammatory foci detected in H&E sections is shown in FIG. 8 and the average demyelination score from Luxol fast blue sections shown in FIG. 9.

Consistent with the clinical findings, the histological readouts in these mice were indicative of significantly less severe disease than in the vehicle-treated mice. Fewer inflammatory foci were found in the RHB 104 treated mice than in sections from vehicle treated mice. In addition, the inflammatory foci were smaller in the RHB-104 treated mice than in vehicle treated mice.

Demyelinated areas were significantly smaller in the RHB-104 treated mice than in vehicle treated mice. All these findings confirm the clinical observation that RHB-104 treated mice had significantly less severe EAE than vehicle-treated mice at the end of the MS mouse model study.

Experiment 3

EAE Relapse Study

The model most strongly resembles the remitting-relapsing form of MS (the most common form of MS).

As a background to the model, it is to be understood that mice develop a first episode of paralysis 11-14 days after immunization in an EAE model and, similar, to most MS patients, they fully or almost fully recover from this first wave of paralysis. After a disease-free period of 1-2 weeks, 50 to 100% of the mice develop a second wave of paralysis (relapse).

This model is used for testing the effect of compounds on the development of EAE relapses (therapeutic treatment). Treatment can be initiated at the onset of clinical signs of EAE, or at the start of recovery from the first wave of EAE. This model is typically run for 5 to 7 weeks, but mice are sometimes observed longer Experiment Design Disease was induced by immunizing mice on Day 0 with $PLP_{139-151}$ peptide emulsified in complete Freund's adjuvant (CFA).

To assess disease development, mice were weighed three times per week (Monday, Wednesday and Friday) from the time of immunization and scored daily for clinical signs of EAE starting on Day 9.

Enrollment of mice into groups occurred on the second day of clinical signs of EAE for each mouse. Mice were enrolled into treatment groups as they develop signs of EAE (rolling enrolment).

Group Assignment and Treatment

All mice were initially considered a single group. Daily scoring started on Day 9 after immunization.

Enrolment of mice into groups occurred on the second day of clinical signs of EAE for each mouse. Mice were enrolled into treatment groups as they develop signs of EAE (rolling enrolment).

45 mice were enrolled into 3 groups of 15 and the treatment started on the day of enrolment. Assignment was balanced to achieve similar scores between the groups at enrolment.

7 mice which develop disease latest, or which had unusual symptoms, were not enrolled into groups and were not used in the study.

Groups

Group 1—Vehicle (PBS), p.o., BID, 5 mL/kg (negative control)

Group 2—treated with FTY-720 (Fingolimod, Gilenya) 3 mg/kg, p.o., QD (a drug used for treatment of MS and used as a positive control)

Group 3—treated with RHB-104, p.o., BID, 5 mL/kg

Treatment

Treatment started on the day of enrolment and continued until Day 39.

All dosing was performed at the same time (+/−1 hour) each day. There was at least 10 hours between morning and evening dosing and not more than 14 hours between evening and morning dosing.

The last day of dosing was Day 39 for all mice.

Scoring and Readout

Mice were scored daily from Day 9 to Day 40, and body weight was measured three times/week (Monday, Wednesday and Friday), starting before immunization (Day −1).

Scoring was performed blind, by a person unaware of both treatment and of previous scores for each mouse.

Readouts were EAE scores on the scale 0-5 in 0.5 unit increments, and changes in body weight.

EAE Scoring

EAE was scored on scale 0 to 5 as described above.

Statistical Analysis

Statistical analysis was performed as follows:

Median day of EAE onset compared using Wilcoxon's survival test

Mean day of EAE onset compared using two-tailed Student's t-test

Mean maximum score (MMS) of first wave compared using Wilcoxon rank sum test

Relapse incidence compared using Chi-square test

Mean maximum score (MMS) of relapse compared using Wilcoxon rank sum test

End score compared using Wilcoxon rank sum test

Change in body weight compared using two-tailed Student's t-test

Results 8 mice in Group 1 showed relapse as indicated in their clinical scores whereas only 2 mice from each of Groups 2 and 3 demonstrated relapse.

Figure 12:
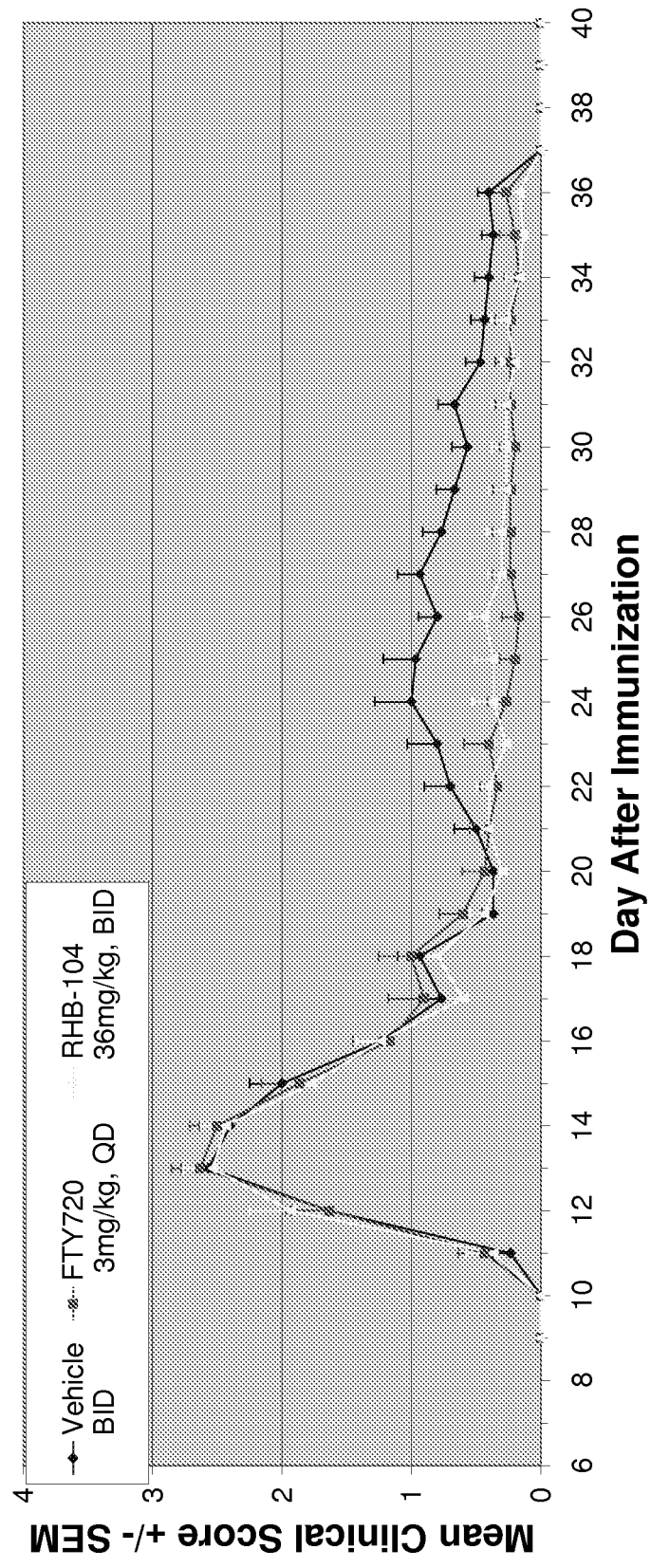
FIG. 12 is a graph showing the severity of relapse disease in various treatment groups of a recognised mouse model.

Further, the severity of the relapse disease in Group 3 was significantly less than the severity in Group 1 as evidenced by the graph shown in FIG. 12.

CONCLUSION

In addition to reducing the symptoms in an initial onset of EAE, the present RHB-104 composition has been shown to protect against relapse of the disease in the well recognised mouse model used above and in the cases where relapse occurs, the severity of the disease is significantly reduced when compared to a negative control group. Collectively, these results indicate that RHB-104 was highly efficacious in reducing disease severity in this study.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of treating a subject suffering from relapsing-remitting multiple sclerosis comprising:
    administering, to the subject for an effective treatment period, single dosage forms of 45 mg rifabutin co-formulated with 95 mg clarithromycin and 10 mg clofazimine,
    wherein administration of the single dosage forms over the effective treatment period protects against a relapse episode.

2. The method of claim 1 wherein the single dosage forms further comprises an antibiotic selected from the group consisting of daptomycin, clindamycin, rifampicin, erythromycin, oleandomycin, roxithromycin, azithromycin, kanamycin, gentamycin, tobramycin, streptomycin, neomycin, paromomycin, ethambutol, isoniazid, minocyclin, and tetracycline.

3. The method of claim 1 wherein the single dosage forms further comprises Vitamin D.

4. The method of claim 1 wherein the single dosage forms further comprises an anti-inflammatory agent.

5. The method of claim 1 wherein the single dosage forms further comprises an anti-inflammatory agent selected from one or a combination of 5-aminosalicylic acid, azathioprine or methotrexate.

6. The method of claim 1 wherein the clofazimine in the single dosage forms is dispersed in an absorption enhancer.

7. The method of claim 1 wherein the clofazimine in the single dosage forms is dispersed in polyethylene glycol.

8. The method of claim 1 wherein the single dosage forms are administered to the subject orally.

9. The method of claim 1 wherein the single dosage forms effect proinflammatory cytokines in the subject.

10. The method of claim 1 wherein, upon administration to the subject, a reduction in demyelination is observed.

11. The method of claim 1 wherein the subject is or is not infected with *Mycobacterium* paratuberculosis.

* * * * *